United States Patent [19]
Soudant et al.

[11] Patent Number: 5,436,230
[45] Date of Patent: Jul. 25, 1995

[54] USE OF A GROWTH FACTOR IN A SLIMMING COMPOSITION

[75] Inventors: Etienne Soudant, Fresnes; Jean-Francois Nadaud, Paris, both of France

[73] Assignee: L'Oreal, Paris, France

[21] Appl. No.: 90,202

[22] PCT Filed: Jan. 14, 1992

[86] PCT No.: PCT/FR92/00026
§ 371 Date: Sep. 8, 1993
§ 102(e) Date: Sep. 8, 1993

[87] PCT Pub. No.: WO92/11838
PCT Pub. Date: Jul. 23, 1992

[30] Foreign Application Priority Data

Jan. 14, 1991 [FR] France .................... 91 00324

[51] Int. Cl.$^6$ ............ A61K 31/00; A61K 31/48; A61K 31/245; A61K 31/175
[52] U.S. Cl. .................................. 514/21; 514/12
[58] Field of Search .............. 514/12, 21, 910–912

[56] References Cited

U.S. PATENT DOCUMENTS

| | | | |
|---|---|---|---|
| 4,525,359 | 6/1985 | Greenway, III | 514/250 |
| 4,645,828 | 2/1987 | Twardzik | 530/325 |
| 5,030,451 | 7/1991 | Trebosc | 424/401 |
| 5,180,820 | 1/1993 | Barde | 530/412 |
| 5,215,759 | 6/1993 | Mausner | 424/491 |

FOREIGN PATENT DOCUMENTS 2472385  7/1981  France .
2533438  3/1984  France .

OTHER PUBLICATIONS

Carpenter, G. et al., "Epidermal Growth Factor", *Ann. Rev. Biochem.* (1979), 48:193–216.

King, L., "Progress in Dermatology", vol. 19, No. 1, Mar. 1985, pp. 1–8.

Gospodarowicz, G., "Fibroblast Growth Factor: Structural and Biological Properties", *J. of Cell. Phys. Supplement.* 5:15–26 (1987).

Shipley, G. et al. "Growth of Normal Human Keratinocytes and Fibroblasts in Serum–Free Medium is Stimulated by Acidic and Basic Fibroblast Growth Factor", *J. of Cell. Phys.*, 138–511–518 (1989).

Barritault, D. et al., "Purification, Characterization, and Biological Properties of the Eye–Derived Growth Factor from Retina: Analogies with Brain–Derived Growth Factor", *Journal of Neuroscience Research*, 8:477–490 (1982).

Fourtainer, A. et al. "Eye–Derived Growth Factor Isolated from Bovine Retina and Used for Epidermal Wound Healing in Vivo", *The Journal of Investigative Dermatology*, vol. 87, No. 1, Jul. 1986, pp. 76–80.

Tran et al., European J. of Pharmacology, vol. 76, pp. 435–438 (1981).

The Merck Manual of Diagnosis and Therapy, 5th ed., Robert Berkow, Editor, Merck and Co., Inc. Rahway, N.J. 1987, pp. 950–955.

O'Sullivan, U., et al., "Insulin–like Growth Factor–1 (IGF–1) in Mice Reduces Weight Loss During Starvation", *Endocrinology*, vol. 125, No. 5, Nov. 1989, The Endocrine Society (U.S.), pp. 2793–2794.

*Primary Examiner*—Jill Warden
*Assistant Examiner*—Lynn Touzeau
*Attorney, Agent, or Firm*—Oliff & Berridge

[57] ABSTRACT

Utilization of a growth factor as active principle of a slimming and lipolytic composition and its utilization in a treatment method particularly in the process for improving the aesthetic aspect of the skin. The slimming composition may also contain the growth factor in association with a lipolytic substance such as caffine.

31 Claims, 1 Drawing Sheet

USE OF A GROWTH FACTOR IN A SLIMMING COMPOSITION

The subject of the present invention is the use of a growth factor as the active principle in the preparation of a slimming and lipolytic composition and its application in a method of treatment for improving the aesthetic appearance of the skin. The present invention is also directed to a slimming composition containing a growth factor combined with another lipolytic substance such as caffeine.

BACKGROUND OF THE INVENTION

Growth factors are polypeptide molecules shown by in vivo and in vitro studies to multiply and differentiate cells of different origins and species. For some of these growth factors, it has been possible to determine the amino acid sequence and the structure of the corresponding gene. Among tissue growth factors, which were studied in depth because of the multiplicity of the target cells concerned, or the biological effects observed, and because of the therapeutic impact that physicians and particularly dermatologists may expect, it should be mentioned in particular, Epidermal Growth Factor (EGF), Fibroblast Growth Factor (FGF) and Eye Derived Growth Factor (EDGF).

The expression "growth factor" is also understood to mean mixtures of growth factors, particularly that derived from nerve tissue, hereinafter called m-NTGF (mixture of Nervous Tissue Growth Factors) as well as other peptides or polypeptides with a growth factor character of natural or synthetic origin.

Growth factors have a stimulating effect on cell proliferation, particularly that of epithelial cells, and have proved effective in the scarring of lesions.

Some of these growth factors are used in cosmetology for skin care as described for example in French Patent Application No. 79.31731 (Publication No. 2.472.385) and particularly in its Certificate of Addition No. 82.15559 (Publication No. 2.533,438). However, in these references their mitogenic activity is assumed to render these factors useful in skin care.

The studies on EGF that may be mentioned in particular are the articles by G. Carpenter et al., Ann. Rev. Biochem., 48, 193–216 (1979) and L. E. King et al., Progress in Dermatology, Vol. 19, No. 1, 1–8 (1985).

Among the studies on FGF, particular mention may be made of the articles by D. Gospodarowicz et al., J. Cell, Physiol. Supp., 5/15-26 (1987), and Gary D. Shipley, et al., J. Cell. Physiol. 138/511–518 (1989).

Among the articles on EDGF, reference may be made to the articles by D. Barritault, et al., Journal of Neuroscience Research, 8:477–490 (1982) and A. Y. Fourtanier, et al., The Journal of Investigative Dermatology, Vol. 87, No. 1, 76–80 (1986).

It has now been discovered quite unexpectedly that these growth factors have a lipolytic effect and can be used as active principles in slimming compositions.

It has been found in particular that these growth factors may be used to combat cellulitis and local fat overload.

It is known that swelling of the subcutaneous connective tissue, known as cellulitis, gives the skin an "upholstered" appearance. Cellulitis is formed by local accumulation of fat and water trapped in a matrix of more or less fluid-tight compartments.

BRIEF DESCRIPTION OF THE DRAWINGS

Topical application of an anticellulitic agent may erase local accumulation of fat by lipolytic action. The best-known and most widespread method of stimulating lipolysis is by inhibiting phosphodiesterase to prevent or at least limit the rate of cyclic AMP breakdown. Phosphodiesterase destroys cyclic AMP converting it into 5' AMP so that it is unable to activate lipolysis. Hence the point is to inhibit the action of phosphodiesterase to achieve a high level of cyclic AMP in the adipocytes in order to stimulate lipolytic activity.

Among the various phosphodiesterase inhibitors recommended as slimming agents, xanthine bases, particularly caffeine, may be mentioned in particular. However, caffeine, particularly at high concentrations, is not always tolerated, even topically, because it penetrates and may give rise to palpitations in certain particularly sensitive subjects. It has now been quite unexpectedly discovered that growth factors are excellent substitutes or supplements for caffeine. Thus, without limiting the scope of the invention, it is assumed that growth factors owe their lipolytic effect to an action mechanism different from that of caffeine.

SUMMARY OF THE INVENTION

Figure 1:
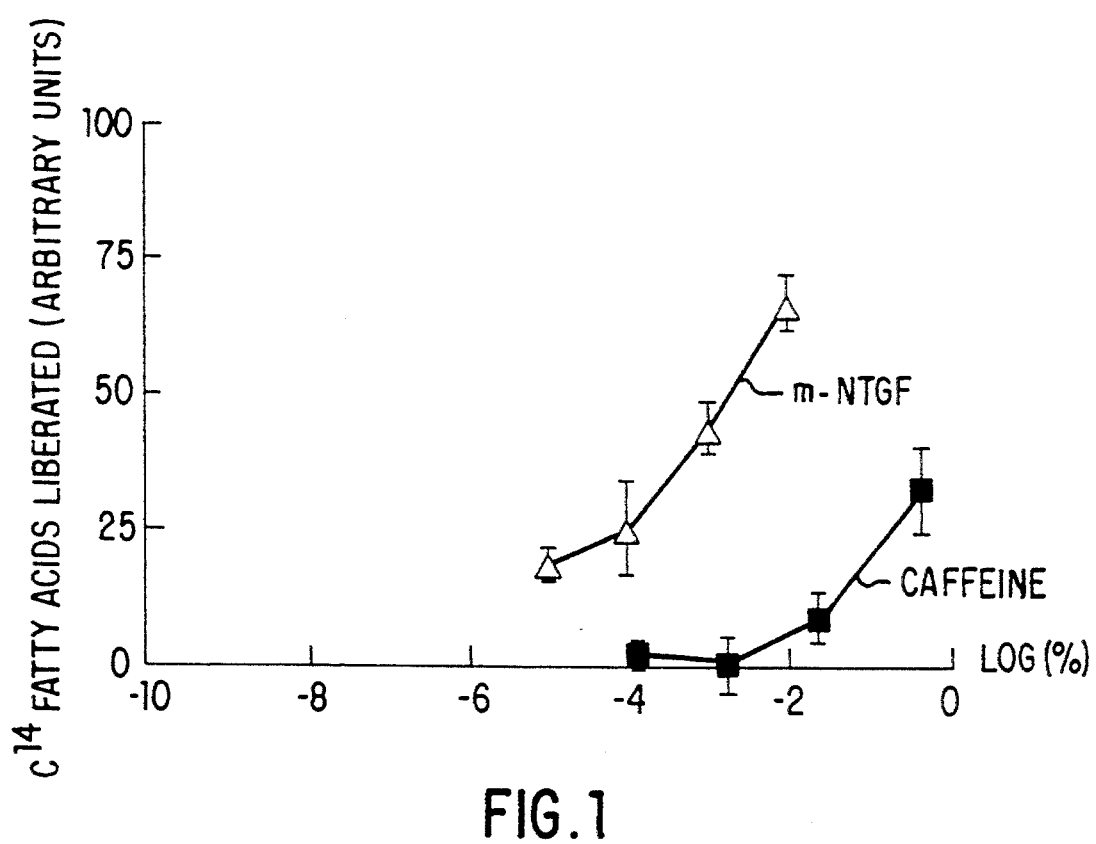

A primary object of the present invention is the use of a growth factor in the preparation of a slimming composition for topical or oral administration. These compositions may contain growth factors alone or in combination with other lipolytic agents such as for example xanthines, particularly caffeine, or alpha-tocopherol nicotinate, cola extract, carnitine, and vitamin E and its acetate. Thus, in the case of caffeine-based compositions, utilization of which may cause problems, it is possible to introduce a growth factor and reduce the necessary dose of caffeine while retaining a good lipolytic effect.

A further object of the present invention is a slimming composition characterized by containing in combination at least one growth factor and another lipolytic substance, preferably caffeine.

DETAILED DESCRIPTION OF THE INVENTION

FIG. 1 shows the results of this study as a function of the quantity of radioactivity found in the fatty acids released by lipolysis.

Among the growth factors that can be used according to the present invention, all the above-listed growth factors can be cited. Preferably, a mixture of factors such as m-NTGF can be used.

The m-NTGF factors are obtained from whole brains or brain fractions, of various origins, after enzymatic or physical-chemical hydrolysis and molecular screening to collect the fragments with molecular weights corresponding to those of growth factors.

Other slimming substances may also be used according to the invention. Oily water-soluble or water-alcohol plant extracts may be cited.

Among the oily plant extracts, the following extracts may be cited:

Climbing ivy (Hedera helix) extract obtained, for example, by prolonged soaking of the leaves in propylene glycol;

Arnica (Arnica montana L) extract obtained, for example, by soaking the capitula of the arnica flowers in glycol or apricot oil;

Rosemary (Rosmarinus officinalis N) extract obtained, for example, by prolonged soaking of the leaves in glycol or apricot oil;

Marigold (Calendula officinalis) extract obtained, for example, by prolonged soaking of the flowers in glycol or apricot oil;

Sage (Salvia officinalis L) extract obtained, for example, by prolonged soaking of the leaves in glycol or apricot oil;

Ginseng (Panax ginseng) extract obtained, for example, by soaking the ginseng roots in a neutral oil;

St.-John's-wort (Hypericum perforatum) extract obtained, for example, from the flowers by soaking in a neutral oil or glycol;

Butcher's-broom extract obtained, for example, from butcher's-broom (Ruscus aculeatus L) rhizomes ground and extracted in a water-alcohol solution of an alcohol having 3 to 6 carbon atoms, preferably water-saturated n-butanol;

Meadowsweet (Filipendula ulmaria L) extract obtained, for example, by prolonged soaking of the whole plant in a neutral oil or in isopropyl myristate;

Orthosiphon (Orthosiphon staminicus Benth) extract obtained, for example, by prolonged soaking of the floral capitula in a neutral oil;

Alga (Fucus vesiculosus) extract obtained, for example, by prolonged soaking of the whole plants in an oxyethylenated oil.

Among the water-soluble extracts, the following extracts may be cited:

Water-soluble algae extract, water-glycol extract obtained, for example, by prolonged soaking of Fucus vesiculosus thalli;

The water-soluble extract of climbing ivy (Hedera helix), a water-glycol extract obtained, for example, by prolonged soaking of the leaves and stems;

The water-soluble extract of birch (Betula alba), a water-glycol extract obtained, for example, by prolonged soaking of the bark.

Among the water-alcohol extracts, the following extract may be cited:

The water-alcohol extract of the cola nut (Cola nipida) obtained, for example, by leaching the seeds in alcohol.

According to the invention, the growth factor is generally present in a concentration of between 0.01 and 25% by weight, preferably between 0.5 and 10 wt. % relative to the total weight of the composition.

When these compositions are administered topically, they may be in various forms, particularly in the anhydrous form such as an oil or ointment, or in the form of an O/W or W/O emulsion with the appearance of a cream or milk, or in the form of a gel and also in the form of lipid vesicles made of ionic lipids (liposomes) or nonionic lipids.

When the compositions according to the invention are administered orally, they may be in the form of tablets, capsules, coated pills, syrups, suspensions or solutions.

When the composition is in the anhydrous form, the excipient may be a vegetable or animal oil, a mineral oil, a synthetic oil, or mixtures of these oils.

Among the vegetable or animal oils, modified or unmodified, the following may be cited as examples: sweet almond oil, avocado oil, olive oil, jojoba oil, perhydrosqualene, calophyllum oil, lanolin and its derivatives, sunflower oil, wheat-germ oil, sesame oil, peanut oil, grapeseed oil, soy oil, rapeseed oil, safflower oil, coconut oil, corn oil, hazelnut oil, karite butter, Shorea robusta oil, palm oil and apricot oil.

Among the mineral oils, Vaseline oil may be employed, and among the synthetic oils: ethyl and isopropyl palmitates, alkyl myristates such as isopropyl, butyl, and cetyl myristate, hexyl stearate, octanoic and decanoic acid triglycerides (for example the product sold under the name "Miglyol" by the Dynamit Nobel Company), cetyl ricinoleate, stearyl octanoate (purcelin oil), and hydrogenated polyisobutene as well as waxes such as ozokerite may be used.

The fatty excipient can also contain certain compounds considered as fats such as long-chain alcohols such as cetyl alcohol, stearyl alcohol, myristic alcohol, hydroxystearyl alcohol, oleic alcohol, and isostearyl alcohol.

When the compositions are in the form of an emulsion, the fatty phase of the emulsion represents 10 to 80 wt. %, the water phase 15 to 80%, and the emulsifier 5 to 30 wt. % relative to the total weight of the emulsion.

When the compositions are in the form of vesicles, the active principle, when it is fat-soluble, is encapsulated in the lipid lamellar phase and in the aqueous phase when the active principle is water-soluble.

The compositions according to the invention can also contain various conventional ingredients such as for example surfactants, emollients, thickeners, polymers, silicone oils, fragrances, dyes, sweeteners, antioxidants, or preservatives.

Among the silicone oils, cyclopentadimethylsiloxane, particularly the product sold under the name "Volatile Silicone 7158" by the Union Carbide Company as well as alkyldimethicone copolyol, particularly the product sold under the name "Abil We 09" by the Goldschmidt Company, are preferably used.

The surfactants preferably used are glycerin monostearate, particularly the product sold under the name "Arlacel 165" by the Atlas Company, as well as sorbitan monostearate oxyethylenated (OE) with the aid of 20 moles of OE, particularly the product sold as "Tween 60" by the Atlas Company, or a surfactant mixture sold under the commercial name "Protegin X" by the Goldschmidt Company.

The emollients preferably used are polymers of ethylene oxide, glycerol cocoate oxyethylenated with 7 moles of OE, particularly the product sold under the name "Cetiol HE" by the Henkel Company as well as the mixture of glycol stearate and polyethylene glycol (PEG 6 and 32), particularly the product sold under the name "Tefose 63" by the Gattefosse Company.

The thickeners preferably used are silica derivatives such as pyrogenated colloidal silica, particularly the product sold under the name "Aerosil 200" by the Degussa AG Company as well as crosslinked polyacrylic acid, particularly the products sold under the names "Carbopol 940" and "Carbopol 941" by the Goodrich Company.

A still further object of the present invention is a treatment method designed to combat cellulitis and local fat overload and to improve the aesthetic appearance of a person, characterized by application to the skin or oral administration of a composition containing at least one growth factor as the lipolytic active principle.

The treatment method according to the invention is generally conducted over a period of 1 to 35 weeks with 1 to 3 applications or administrations per day. In the case of oral administration, the dosage may be for example 1 to 10 (400 mg) capsules (containing 100 mg of active principle each) per day depending on the body weight of the person to be treated.

Study of Lipolytic Effect

The techniques of incorporating the $C^{14}$-labeled lipid precursors such as sodium acetate allow the kinetics of lipid production and release by the cells producing them to be monitored and the influence of various factors or active substances to be studied. The lipids produced by these cells are radiolabelled by providing such precursors to lipid-producing cells. The same cells, whose lipids are radiolabelled, can then be subjected to lipolysis by the action of a lipolytic agent that releases the quantifiable radioactive elements.

In order to demonstrate the lipolytic activity of the growth factors used according to the present invention, a mixture of growth factors from the pituitary gland was taken and its lipolytic activity compared in vitro to that obtained by caffeine as a known lipolytic substance.

The study of the lipolytic effect of these active substances was performed on cultured fat cells which, contrary to adipocytes isolated from fatty tissue which cease to be viable after a few hours, can be stored for up to three weeks with no loss of viability (Alihaud G., Mol. Cell. Biochem. 49 (1982) 17–31). Differentiated rat Ob 17 cells cultured under specific conditions were used (Gaillard D. et al. Biochim. Biophys. Acta, 846 185-91 (1985) and Doglio A. et al. Biochem. J. 238 123–129 (1986) ).

The lipolysis experiments were conducted after exposure of the cells to $C^{14}$-labeled acetate (two periods of 48 hours in the presence of 0.5 $\mu$Ci/dish). Under steady-state conditions, the radioactivity was found principally in the triglyceride fatty acids (Negrel R. et al. Proc. Natl. Acad. Sci. USA, 75 6054–6058 (1978), and Forest C. et al. Exp. Cell. Res. 168 218-232 (1987)).

The lipolysis tests were conducted at 37° C. as a function of time with two dishes per concentration and a minimum of four kinetic points per dish.

Thus each substance was studied for dose-response (six concentrations per active substance at the various powers of ten between $10^8$ and $10^3$M).

FIG. 1 shows the results of this study as a function of the quantity of radioactivity found in the fatty acids released by lipolysis. In FIG. 1, the maximum value of 100 arbitrary units corresponds to isoproterenol activity at a concentration of $10^7$ M. This activity is so low that approximately 1% of this maximum activity can be deemed satisfactory. However, activity of at least 10% is preferred, and more particularly 15% of said maximum value.

As a function of the curves, it is evident that the mixture of growth factors according to the invention triggers release of fatty acids demonstrating a greater lipolytic activity than that of caffeine, particularly at a far lower concentration.

Examples of compositions with a slimming action containing one or more growth factor(s) in combination will now be provided for illustration with no limiting nature.

EXAMPLE 1

| | |
|---|---|
| m-NTGF | 0.05 g |
| Ozokerite | 10.0 g |
| Isopropyl palmitate | 10.0 g |
| White Vaseline | 15.0 g |
| Preservative | 0.2 g |
| Antioxidants | 0.30 g |
| Oily calendula extract | 5.0 g |
| Oily Fucus extract | 10.0 g |
| Oily ivy extract | 10.0 g |
| Oily arnica extract | 5.0 g |
| Aromatic composition | 1.0 g |
| Vaseline oil qs | 100.0 g |

EXAMPLE 2

| | |
|---|---|
| m-NTGF | 1.00 g |
| Carbopol 940 | 0.90 g |
| Ethyl alcohol | 20.00 g |
| Triethanolamine | 0.2 g |
| Glycerin | 5.0 g |
| Fragrance | 0.3 g |
| Water-soluble birch extract | 3.0 g |
| Water-soluble ivy extract | 4.0 g |
| Water-soluble algae extract | 4.0 g |
| Water-soluble cola nut extract | 4.0 g |
| Preservative | 0.3 g |
| Caffeine | 2.0 g |
| Water qs | 100.0 g |

EXAMPLE 3

Slimming O/W Emulsion

| | |
|---|---|
| m-NTGF | 20.0 g |
| Volatile silicone 7158 | 10.0 g |
| Perhydrosqualene | 18.0 g |
| Vaseline oil | 5.0 g |
| Liquid lanolin | 4.0 g |
| Arlacel 165 (Atlas) | 6.0 g |
| Tween 60 (Atlas) | 2.0 g |
| Cetyl alcohol | 1.2 g |
| Stearic acid | 2.5 g |
| Triethanolamine | 0.1 g |
| Preservative | 0.3 g |
| Antioxidants | 0.3 g |
| Fat-soluble St. John's-wort extract | 4.0 g |
| Fat-soluble orthosiphon | 3.0 g |
| Fat-soluble ivy | 4.0 g |
| Fat-soluble arnica | 4.0 g |
| Water qs | 100.0 g |

EXAMPLE 4

Slimming W/O Emulsion

| | |
|---|---|
| EGF | 5.0 g |
| Protegin X | 20.0 g |
| Vaseline oil | 10.0 g |
| Glycerin | 5.0 g |
| Magnesium sulfate | 0.5 g |
| Oily calendula extract | 5.0 g |
| Oily sage extract | 5.0 g |
| Oily algae extract | 8.0 g |
| Oily rosemary extract | 3.0 g |
| Aromatic composition | 1.0 g |
| Preservative | 0.3 g |
| Water | 100.0 g |

EXAMPLE 5

Slimming O/W Emulsion

| | |
|---|---|
| m-NTGF | 0.01 g |
| Caffeine | 1.0 g |
| Propylene glycol | 2.0 g |

| | |
|---|---|
| PEG 400 | 3.0 g |
| Preservative | 0.3 g |
| Carbopol 941 | 0.2 g |
| Isopropyl myristate | 1.0 g |
| Cetyl alcohol | 3.0 g |
| Stearic acid | 3.0 g |
| Glycerol monostearate | 3.0 g |
| Corn germ oil | 2.0 g |
| Oily arnica extract | 5.0 g |
| Butcher's-broom saponins | 1.0 g |
| Water-soluble algae extract | 2.0 g |
| Water-soluble ivy extract | 3.0 g |
| Meadowsweet herbasol | 3.0 g |
| Fragrance | 0.50 g |
| Mineralized water qs | 100.0 g |

EXAMPLE 6

Slimming O/W Emulsified Gel

| | |
|---|---|
| EDGF | 0.5 g |
| Carbopol 940 | 0.6 g |
| Volatile silicone 7158 | 3.0 g |
| Purcelin oil | 7.0 g |
| Tefose 63 | 3.0 g |
| Preservative | 0.3 g |
| Ethyl alcohol | 15.0 g |
| Fragrance | 0.4 g |
| Triethanolamine | 0.2 g |
| Oily algae extract | 6.0 g |
| Oily arnica extract | 6.0 g |
| Oily ivy extract | 6.0 g |
| Oily rosemary extract | 6.0 g |
| Fat-soluble ginseng extract | 4.0 g |
| Alpha-tocopherol nicotinate | 0.05 g |
| Demineralized water qs | 100.0 g |

EXAMPLE 7

Liposome Slimming Cream

| | |
|---|---|
| m-NTGF | 10.0 g |
| Polyglycerolated cetyl alcohol | 3.8 g |
| β-sitosterol | 3.8 g |
| Dicetyl phosphate | 0.4 g |
| Preservative | 0.3 g |
| Sunflower oil | 35.0 g |
| Fragrance | 0.6 g |
| Carbopol 940 | 0.2 g |
| Triethanolamine | 0.2 g |
| Demineralized water qs | 100.0 g |

EXAMPLE 8

Orally Administered Treatment Composition

According to the present invention, gel capsules or capsules with the following unit composition are prepared:

| | |
|---|---|
| m-NTGF | 100.0 mg |
| Aerosol 200 | 5.0 mg |
| Zinc stearate | 5.0 mg |
| Talc | 5.0 mg |
| Lactose qs | 400.0 mg |

We claim:

1. A method of treatment for slimming a body part of a person having local fat overload, said method comprising: administering to said person a slimming effective amount of a composition comprising an effective amount of at least one growth factor that has lipolytic activity.

2. The method of claim 1, wherein said composition is topically administered to said body part.

3. The method of claim 1, wherein said composition is orally administered to said person.

4. The method of claim 1, wherein said growth factor is selected from the group consisting of EGF, FGF, EDGF and m-NTGF.

5. The method of claim 4, wherein said growth factor is m-NTGF.

6. The method of claim 1, wherein said growth factor is present in said composition in a concentration of between 0.01 and 25 wt. % relative to total weight of the composition.

7. The method of claim 6, wherein said growth factor is present in said composition in a concentration of between 0.5 and 10 wt. % relative to total weight of the composition.

8. The method of claim 1, wherein said composition is in a form selected from the group consisting of: a lotion, an oil-in-water emulsion, a water-in-oil emulsion, a gel, a cream, an ointment, an aerosol spray, and a vesicular system.

9. The method of claim 1, wherein said composition comprises at least one ingredient selected from the group consisting of a preservative, a fragrance, an oil, an alcohol, a fatty ester and a vitamin.

10. The method of claim 1 wherein said composition further comprises a lipolytic substance.

11. The method of claim 10, wherein said lipolytic substance is caffeine.

12. The method of claim 1, wherein said growth factor has an activity of approximately 1 to 100% of the lipolytic activity of isoproterenol.

13. A topical composition for slimming a body part of a person having local fat overload, said composition comprising:

a topical carrier, at least one growth factor having a lipolytic activity and caffeine, said growth factor and said caffeine being present in a slimming effective amount.

14. The topical composition of claim 13, wherein said growth factor is selected from the group consisting of EGF, FGF, EDGF and m-NTGF.

15. The topical composition of claim 14, wherein said growth factor is m-NTGF.

16. The topical composition of claim 13, wherein said growth factor is present in a concentration of between 0.01 and 25 wt. % relative to total weight of the composition.

17. The topical composition of claim 16, wherein said growth factor is present in a concentration of between 0.5 and 10 wt. % relative to total weight of the composition.

18. The topical composition of claim 13, wherein said composition is in a form selected from the group consisting of a lotion, an oil-in-water emulsion, a water-in-oil emulsion, a gel, a cream, an ointment, an aerosol spray, and a vesicular system.

19. The topical composition of claim 13, wherein said composition comprises at least one ingredient selected from the group consisting of a preservative, a fragrance, an oil, an alcohol, a fatty ester and a vitamin.

20. The topical composition of claim 13, wherein said growth factor has an activity of approximately 1 to 100% of the lipolytic activity of isoproterenol.

21. An oral composition for slimming a body part of a person having local fat overload, said composition comprising:

a oral carrier, at least one growth factor having a lipolytic activity and caffeine, said growth factor and said caffeine being present in a slimming effective amount.

22. The composition of claim 21, wherein said growth factor is selected from the group consisting of EGF, FGF, EDGF and m-NTGF.

23. The composition of claim 21, wherein said growth factor is m-NTGF.

24. The composition of claim 21, wherein said growth factor is present in a concentration of between 0.01 and 25 wt. % relative to total weight of the composition.

25. The composition of claim 21, wherein said growth factor is present in a concentration of between 0.5 and 10 wt. % relative to total weight of the composition.

26. The composition of claim 21, wherein said composition is in a form selected from the group consisting of a lotion, an oil-in-water emulsion, a water-in-oil emulsion, a gel, a cream, an ointment, an aerosol spray, and a vesicular system.

27. The composition of claim 21, wherein said composition comprises at least one ingredient selected from the group consisting of a preservative, a fragrance, an oil, an alcohol, a fatty ester and a vitamin.

28. The oral composition of claim 21, wherein said growth factor has an activity of approximately 1 to 100% of the lipolytic activity of isoproterenol.

29. The method of claim 1, wherein said local fat overload comprises cellulitis.

30. The method of claim 13, wherein said local fat overload comprises cellulitis.

31. The method of claim 21, wherein said local fat overload comprises cellulitis.

* * * * *